(12) United States Patent
Roberts et al.

(10) Patent No.: US 6,217,830 B1
(45) Date of Patent: Apr. 17, 2001

(54) METHODS AND APPARATUS FOR SEPARATING FISCHER-TROPSCH CATALYSTS FROM LIQUID HYDROCARBON PRODUCT

(75) Inventors: George W. Roberts, Raleigh; Peter K. Kilpatrick, Cary, both of NC (US)

(73) Assignee: North Carolina State University, Raleigh, NC (US)

(*) Notice: Subject to any disclaimer, the term of this patent is extended or adjusted under 35 U.S.C. 154(b) by 0 days.

(21) Appl. No.: 09/505,216

(22) Filed: Feb. 16, 2000

Related U.S. Application Data

(62) Division of application No. 08/796,375, filed on Feb. 6, 1997, now Pat. No. 6,114,399, which is a continuation of application No. 08/535,760, filed on Sep. 28, 1995, now abandoned, which is a continuation of application No. 08/144,150, filed on Oct. 27, 1993, now abandoned.

(51) Int. Cl.$^7$ ................. B01J 8/20; C07C 27/00
(52) U.S. Cl. ............... 422/140; 422/224; 422/227; 518/700
(58) Field of Search ............... 208/950; 518/700, 518/705, 706, 709, 715; 422/140, 224, 227, 231, 239, 228, 275

(56) References Cited

U.S. PATENT DOCUMENTS

| | | | |
|---|---|---|---|
| 4,162,965 | 7/1979 | Clapper | 208/177 |
| 4,605,678 | 8/1986 | Brennan et al. | 518/700 |
| 5,332,552 | * 7/1994 | Chang | 422/140 |
| 5,348,982 | * 9/1994 | Herbolzheimer et al. | 518/700 |

OTHER PUBLICATIONS

Schehl, R.R., Rose® Process Solves the LaPorte Catalyst/Wax Separation Problem (5051–238A), 1992.

Zhou, PhZ., Status Review of Fischer–Tropsch Slurry Reactor Catalyst/Wax Separation Techniques, *Burns & Roe Services Corp.* (1991).

Eisenbach, W.O., et al., Supercritical Fluid Extraction of Oil Sands and Residues from Oil and Coal Hydrogenation, *Chemical Engineering at Supercritical Fluid Conditions*, vol. 20, pp. 419–433 (1983).

Stutzer, D., et al., Separatin of Finely Dispersed Solids from Low–Volatile Viscous Media by Gas Extraction, *Chemical Engineering at Supercritical Fluid Conditions*, vol. 21, pp. 435–443 (1983).

Kolbel, H., et al., The Fischer–Tropsch Synthesis in the Liquid Phase, *Catal. Rev.–Sci. Enc.*, vol. 21, pp. 225–274 (1980).

McGee, K., A Better Bottom Line from the Bottom of the Barrel, *Rose Supercritical Fluid Technology* (1992).

* cited by examiner

*Primary Examiner*—Sreeni Padmanabhan
(74) *Attorney, Agent, or Firm*—Myers Bigel Sibley & Sajovec

(57) ABSTRACT

A method of separating a Fischer-Tropsch catalyst from the output slurry of a Fischer-Tropsch bubble column reactor, where the slurry comprises Fischer-Tropsch catalyst particles and liquid hydrocarbon product is disclosed. The method comprises contacting a compressed hydrocarbon solvent (e.g., a supercritical hydrocarbon solvent, or liquid hydrocarbon solvent which may be at near supercritical conditions) with the output slurry at a temperature and pressure where the liquid hydrocarbon product is soluble in the solvent to form a concentrated slurry phase containing the catalyst particles, and an enriched solvent phase containing liquid hydrocarbon product. This contacting step is then followed by the step of separating the concentrated slurry from the enriched solvent. Apparatus for carrying out the method of the invention is also disclosed.

6 Claims, 2 Drawing Sheets

METHODS AND APPARATUS FOR SEPARATING FISCHER-TROPSCH CATALYSTS FROM LIQUID HYDROCARBON PRODUCT

This application is a Division of Ser. No. 08/796,375 filed Feb. 6, 1997 now U.S. Pat. No. 6,114,399, which is a con of Ser. No. 08/535,760 filed Sep. 28, 1995, abandoned, which is a con of Ser. No. 08/144,150 filed Oct. 27, 1993, abandoned.

FIELD OF THE INVENTION

The present invention relates to methods of separating Fischer-Tropsch catalysts from the liquid product (wax) of a Fischer-Tropsch slurry bubble column (SBC) reactor.

BACKGROUND OF THE INVENTION

The conversion of synthesis gas—a mixture of hydrogen, carbon monoxide and other gases such as carbon dioxide and methane—into hydrocarbons has been of interest for more than fifty years. This conversion is frequently referred to as the Fischer-Tropsch (F-T) synthesis in honor of the pioneering work of Franz Fischer and Hans Tropsch in the early 1920's (C. Satterfield, *Heterogeneous Catalysis in Industrial Practice*, p. 432–442 (2d Ed. 1991)).

All large-scale F-T reactors built to date have utilized either fixed-bed or fluidized-bed reactors (See, e.g., G. Stiegel, *PETC Review*, p. 14–23 (Fall 1991); *Fischer-Tropsch Synthesis—The SASOL high-efficiency synfuels process*, Sasol Technology (Pty) Ltd., South Africa). However, a good deal of research and development in the United States, the United Kingdom, and Germany has been devoted to a different reactor concept known as the slurry bubble column (SBC) reactor. (See, e.g., H. Kolbel and M. Ralek, *Catal. Rev.-Sci. Eng.*, 21, 225 (1980)).

Slurry bubble column reactors have distinct advantages over fixed and fluidized bed reactors. Some of these advantages are generic, e.g., a very close approach to isothermal operation, simple construction leading to low capital cost, and the ability to continuously withdraw and add catalyst in order to maintain a constant level of catalyst activity in the reactor. A major advantage that is specific to F-T chemistry, and related reactions such as alcohol synthesis, is the ability of SBC reactors to operate with a feed gas that contains a high ratio of carbon monoxide to hydrogen. Such $CO/H_2$ ratios are characteristic of modern, thermally-efficient coal gasifiers. The use of a SBC reactor in conjunction with a thermally-efficient coal gasifier can lead to a significant reduction in the cost of producing hydrocarbon liquids from coal, and in the overall thermal efficiency of the coal-to-liquids process, relative to current commercial technology.

An important and difficult problem which must be overcome before SBC reactors can be widely used is separating the small catalyst particles in the viscous slurry from the liquid hydrocarbon product. This separation is essential to the commercial implementation of F-T technology based on slurry bubble column reactors for several reasons. First, the liquid product from F-T synthesis must undergo further processing in catalytic reactors. The presence of catalyst particles in the liquid interferes with subsequent processing steps such as hydrocracking and distillation. Second, the portion of the catalyst slurry that is withdrawn for either regeneration or disposal should be as concentrated as possible in order to minimize the amount of valuable hydrocarbon liquid that must be processed during catalyst regeneration or disposal.

P. Zhou, *Status Review of Fischer-Tropsch Slurry Reactor Catalyst/Wax Separation Techniques*, Burns and Roe Service Corp. (February 1991) recently reviewed previous work on F-T slurry catalyst/wax separation, including techniques such as vacuum distillation, thermal cracking of vacuum bottoms, sedimentation, filtration, various forms of centrifugation, high-gradient magnetic separation (HGMS), solvent-assisted catalyst/wax separation and chemical methods. The review concludes that no single technology is entirely satisfactory, and recommends certain "hybrid" approaches. Accordingly, there is a continued need for new methods and apparatus for the separation SBC reactor slurry into F-T catalyst and the hydrocarbon product.

SUMMARY OF THE INVENTION

A first aspect of the present invention is a method of separating Fischer-Tropsch catalyst particles from the output slurry of a Fischer-Tropsch bubble column reactor, the slurry comprising Fischer-Tropsch catalyst particles and liquid hydrocarbon product (those skilled in the art will understand that not all of the liquid in the slurry is net product). The method comprises contacting a compressed hydrocarbon solvent (e.g., a supercritical hydrocarbon solvent, or liquid hydrocarbon solvent which may be at near supercritical conditions) with the output slurry at a temperature and pressure where the liquid hydrocarbon product is soluble in the solvent. This contacting step forms a concentrated slurry phase containing the catalyst particles, and an enriched solvent phase containing liquid hydrocarbon product. The contacting step is then followed by the step of separating the concentrated slurry from the enriched solvent.

Also disclosed is an apparatus for making a hydrocarbon product by a Fischer-Tropsch reaction. The apparatus comprises a Fischer-Tropsch slurry bubble column reactor; a slurry output line connected to the slurry bubble column reactor; a compressed hydrocarbon solvent supply; a contactor connected to the slurry output line and the compressed hydrocarbon solvent supply for contacting compressed hydrocarbon solvent with the output slurry to form a concentrated slurry phase containing the catalyst and an enriched solvent phase containing liquid hydrocarbon product; and a separator connected to the contactor for separating the concentrated slurry from said enriched solvent. In one embodiment, the separator and the contactor are a continuous countercurrent contactor.

As will be explained in greater detail below, an advantage of the present invention is the potential to meet all of the requirements of the separation with a single technology, rather than with a hybrid approach of two different technologies.

Another advantage of the present invention is that it may be practiced with relatively simple apparatus that can be readily assembled from known equipment in a new combination.

Another advantage of the present invention is the capacity for very simple, continuous operation without cyclic operations such as backflushing of filters.

Still another advantage of the present invention is the capacity to fractionate the recovered hydrocarbon product and selectively recycle a lower-molecular-weight cut in order to control the viscosity of the slurry in the SBR reactor.

It is noteworthy that in the recent comprehensive review of F-T slurry catalyst/wax separation techniques (P. Zhou, *Status Review of Fischer-Tropsch Slurry Reactor Catalyst/ Way Separation Techniques,* Burns and Roe Service Corp. (Februaryu 1991)), the use of supercritical extraction is neither described nor suggested. Rather, this review proposes hybrids of multiple techniques.

The foregoing and other objects and aspects of the present invention are explained in detail in the Figures herein and the specification set forth hereinbelow.

DETAILED DESCRIPTION OF THE PREFERRED EMBODIMENTS

The term "hydrocarbon" as used herein generally refers to the products of a Fischer-Tropsch reaction, though the hydrocarbon solvent may be from other sources (as discussed below). The Fischer-Tropsch reaction products are mixtures of predominantly alkanes and alkenes (olefins) which vary widely in molecular weight (e.g., are molecules containing from 1 to 200 carbon atoms or more, depending on the reaction conditions and the structure and composition of the catalyst), and to a lesser extent contain alcohols and other oxygenated molecules, depending on the catalyst and reaction conditions. The ratio of alkanes and alkenes will also depend upon the catalyst employed and the reaction conditions.

Figure 1:
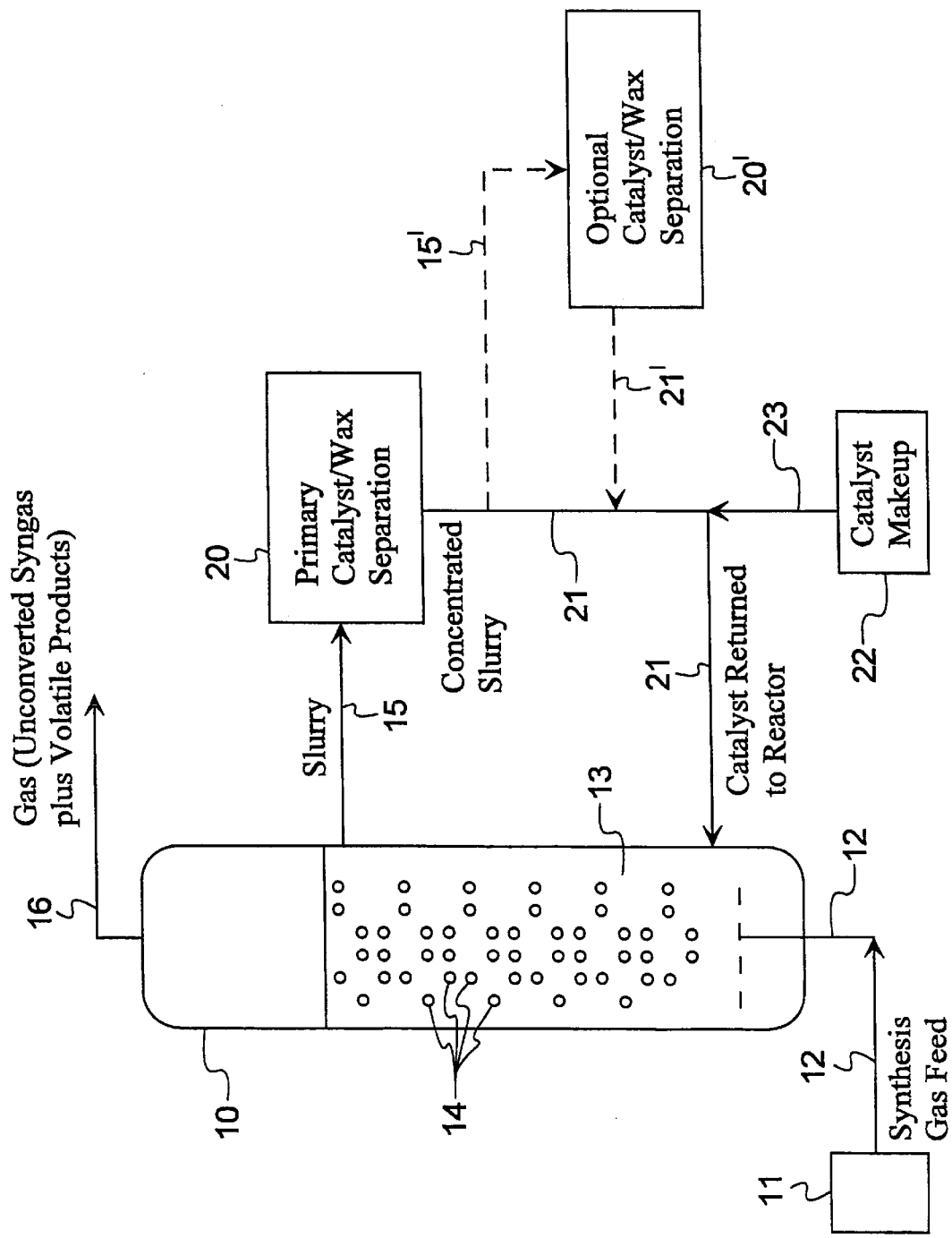
FIG. 1 is a schematic diagram of a Fischer-Tropsch slurry bubble column (SBC) reactor with external catalyst/wax separation.
Figure 2:
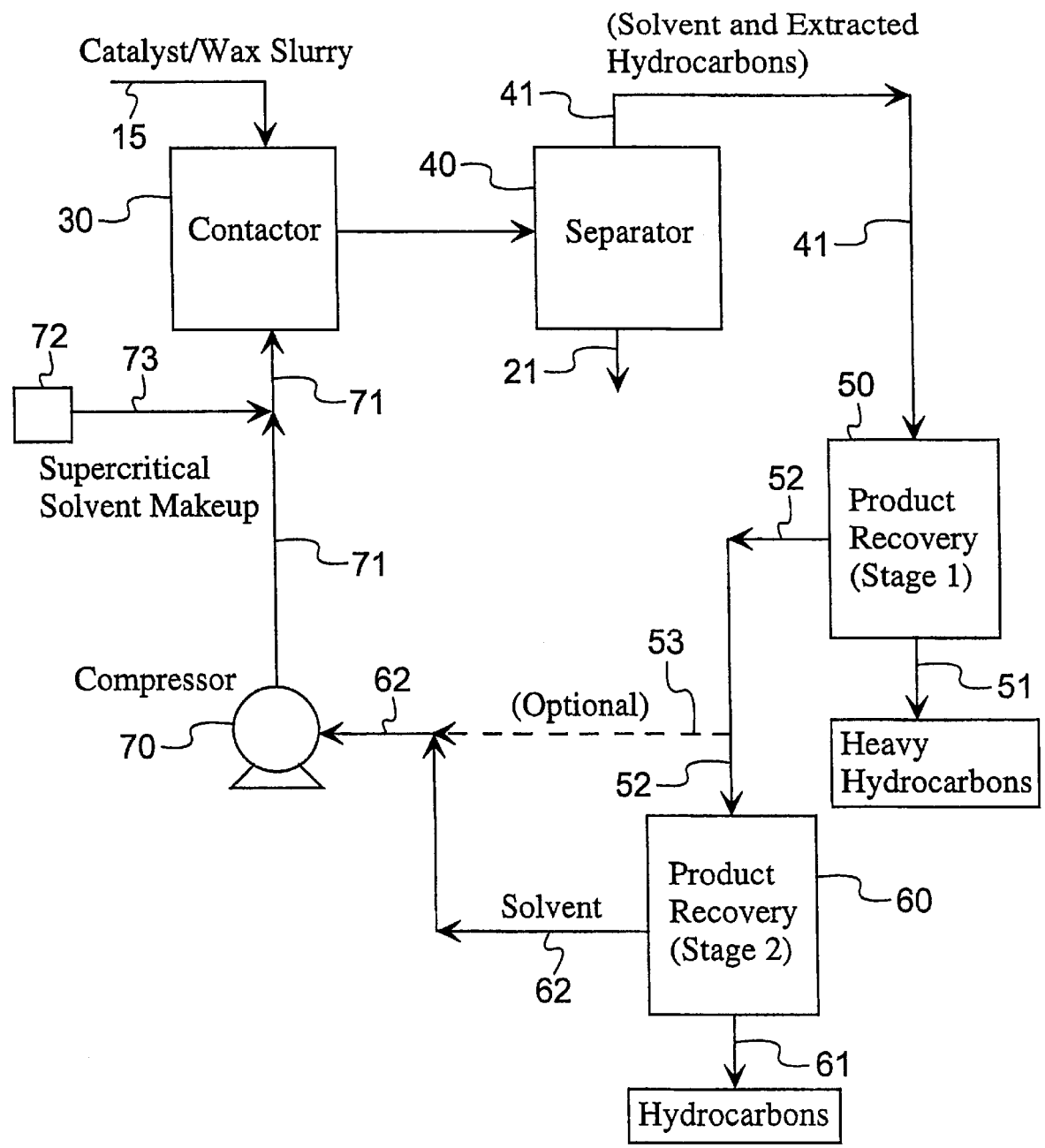
FIG. 2 is a schematic diagram of a Fischer-Tropsch catalyst/wax separator of the present invention as the external catalyst/wax separator of the SBC reactor of FIG. 1.

The present invention may be understood with reference to FIG. 1 and FIG. 2. As shown in FIG. 1, an apparatus for carrying out the present invention comprises a Fischer-Tropsch slurry bubble column reactor 10, which serves to react a synthesis gas in the presence of Fischer-Tropsch catalyst particles to produce a range of products, as described above. Some products are liquid and accumulate in the slurry in the reactor, and other products are gases which exit the reactor with unreacted synthesis gas. The synthesis gas is supplied from a source 11 (e.g., by conversion of coal or natural gas) by a synthesis gas supply line 12. The slurry in the reactor 13 is itself comprised of the liquid hydrocarbon product of the reaction, and the Fischer-Tropsch catalyst particles 14 themselves. Such slurry bubble column reactors are well known (See, e.g., M. Schlesinger et al., *Ind. Eng. Chem.* 46, 1322 (1954); M. Schlesinger et al., *Ind. Eng. Chem.* 43, 1474 (1951); R. Farley and D. Ray, *J. Inst. Pet.* 50, 27 (1964); H. Kolbel and M. Ralek, *Catal. Rev.-Sci. Eng.*, 21, 225 (1980); H. Kolbel and P. Ackermann, *Proc. 3d World Pet. Cong.*, Section IV, pg. 2–4 (1951); H. Kolbel et al., *Proc. 4th World Pet. Cong.*, Section IV/C, pg. 227–247 (1955)). A slurry output line 15 is connected to the slurry bubble column reactor for providing an output of said slurry. A gas outlet line 16 is connected to the reactor for collecting both unconverted synthesis gas and volatile, low molecular weight products of the reaction. The volatile reaction products may be separated from the synthesis gas as a product or used to provide some or all of the hydrocarbon solvent itself, as explained below.

The slurry output line 15 is connected to a primary catalyst/wax separation system 20. The separation system 20 is itself illustrated in greater detail in FIG. 2, and includes a contactor 30 for contacting a compressed hydrocarbon solvent with the output slurry. As also shown in FIG. 2, and discussed in greater detail below, a compressor 70 serves as a compressed hydrocarbon solvent supply means in the catalyst/wax separation system 20, and a separator 40 is connected to or operably associated with the contactor for separating the concentrated slurry from the enriched solvent.

From the separator 40, a concentrated slurry line 21 serves as a recycling means for recycling the concentrated slurry to the Fischer-Tropsch slurry bubble column reactor (see FIG. 1). As shown in FIG. 1, additional catalyst may be added from a catalyst source 22 by line 23 as "makeup", as desired. Typically, at steady state, the same amount of catalyst is withdrawn as is added as makeup.

Preferably the contactor 30 and the separator 40 together comprise a continuous countercurrent extractor (or contactor), though any suitable apparatus may be employed. For example, the contactor 30 may be a mixer, and the separator 40 may be a settler, a centrifuge, or any other suitable apparatus.

The bubble column output slurry generally has a viscosity of about 1 to 20 centipoise when it reaches the contactor for contacting to the solvent. This output slurry may contain from about 10,000 to 400,000 parts per million (ppm) by weight of solid Fischer-Tropsch catalyst particles, with these particles typically being from about 0.1 to 20 microns in diameter. Much smaller particles may also be present, particularly after sustained operation.

Optionally, the system may include a second stage catalyst/wax separation system, as shown by the broken lines in FIG. 1. The second separating system includes a second separation system 20' connected to the first separation system 20 by line 15', and returns concentrated slurry to the bubble column reactor by line 21'. The second separation system may be configured the same as or different from the first separation system, and may be configured so that it is continuously active, capable of operating on a partially active basis, capable of operating in place of the first system, or capable of being switched to an entirely inoperative status. The optional catalyst/wax separation system can be used, among other things, to remove liquid from catalyst that is being disposed of. In general, those skilled in the art will appreciate that numerous additions and alterations can be made to the basic method and apparatus of the particular embodiment of the invention disclosed herein, including the use of three or more separating systems.

As shown in FIG. 2, the enriched solvent leaves the separator 40 and travels through line 41 to a flash tank which serves as the first product recovery stage 50. The product recovery stage provides a means for separating a first fraction of the liquid hydrocarbon product from the enriched solvent to form a first hydrocarbon product fraction, which exits the product recovery stage by line 51, and a first depleted solvent, which exits the product recovery stage by line 52. This first fraction will be the heavy fraction when multiple separating steps are employed. By way of background, such a flash tank is typically an enclosed chamber having an inlet on the top, a liquid outlet on the bottom (by which the first hydrocarbon product fraction exits) and a gas outlet on the top (by which the depleted solvent exits). A valve with a level control is typically provided on the outlet line to insure a continuous pool of liquid at the bottom of the tank and prevent gas from exiting therethrough, a valve control is provided on the inlet line, a pressure control is provided on the gas outlet, and, depending upon the particular separation technique employed, a heat exchanger is optionally provided on the inlet line to elevate the temperature of the enriched solvent. Numerous alternative configurations will be readily apparent to those skilled in the art.

From the product recovery stage 50, the first depleted solvent in line 52 then passes to a second flash tank (which can be configured the same as or different from the first flash tank as discussed above) which serves as a second product recovery stage 60, and which provides a means for separating a second fraction of the liquid hydrocarbon product from the depleted solvent to form a second hydrocarbon product fraction, which exits the second product recovery stage by line 61, and a second depleted solvent, which exits the product recovery stage by line 62. Optionally, bypass line 53 (shown as a broken line) may be provided to bypass the second product recovery stage and return some or all of the first depleted solvent directly to the compressor 70 for recycling to the contactor by line 71 (it being understood that line 53 is not optional when second product recovery stage 60 is absent). Otherwise, the second depleted solvent is returned to the compressor by line 62 for recycling to the contactor. A solvent makeup source 72 may be connected by line 73 which may in turn be connected to line 71 to supply additional solvent to the system, particularly during initiation of the reaction when solvent is not provided by the reaction itself to "prime" the separation process (as discussed further below).

The hydrocarbon solvent may be provided from another source (as noted above), may be comprised at least in part of a fraction of the reaction product (including that produced into the slurry and/or the reaction product produced as a gas) or may consist essentially of a fraction of the reaction product (e.g., may comprise or consist essentially of the second or subsequent liquid hydrocarbon product fractions as described below, the hydrocarbon which remains in the depleted solvent stream after the final product separation step, the reaction product which escapes as gas via line 16, or combinations thereof). Thus, while the solvent may thus be derived from the F-T reaction, the solvent is not the output slurry itself, which has too many heavy components and contains particles. In general, once the system is in operation it produces more than enough product to supply the hydrocarbon solvent for the process, and hence the hydrocarbon solvent may consist essentially of a fraction of the reaction product (i.e., little or no hydrocarbon solvent is supplied from other sources). In a particular embodiment, the hydrocarbon solvent consists essentially of a heavy fraction of the gas reaction product and a light fraction of the liquid reaction product. Typically, the hydrocarbon solvent comprises molecules containing 4 to 12 carbon atoms (e.g., butane, pentane, hexane, heptane, octane, nonane, decane, undecane, dodecane, and alcohols and olefins of the same or similar carbon number), and preferably comprises molecules containing 6 to 8 carbon atoms. The hydrocarbon solvent will typically be a mixture of molecules of different molecular weight, but may if desired be a defined composition consisting essentially of a single molecule of the compositions noted above. The reason that molecules containing 6 to 8 carbon atoms are preferred as the solvent molecules is that solvents of this carbon number have a $T_c$ that is close to the operating T of the bubble column reactor 10. by using such a solvent, the amount of heating (or cooling) of the viscous slurry in line 15 is minimized. Heating or cooling of a viscous slurry containing high solids concentrations is difficult. Once the solvent is selected based on $T_c \approx T_{(reactor)}$, then the operating P of the contactor is essentially determined.

In a preferred embodiment, the solvent is a boiling range fraction (e.g., a range of 10 to 20° C.) of the FT hydrocarbon reaction product, where the critical temperature of the fraction (i.e., as determined by Kay's rule) is close to (e.g., within 50° C. of) the operating temperature of the Fischer-Tropsch bubble column reactor 10. A wider boiling range fraction is employed when more solvent is allowed to remain with the product.

The contacting step is carried out at a temperature and pressure wherein the liquid hydrocarbon product is soluble in the solvent to form a concentrated slurry phase containing the catalyst and an enriched solvent phase containing the liquid hydrocarbon product. Thus the contacting step may be carried out with a supercritical hydrocarbon solvent or a liquid hydrocarbon solvent. When carried out with a liquid hydrocarbon solvent, the solvent is preferably under near-supercritical conditions (e.g., at a temperature and pressure where the density of the solvent is sufficiently increased above the density of the solvent vapor at atmospheric pressure so that the Fischer-Tropsch reaction products to be separated from the catalyst particles are soluble in the solvent). For example, the solvent at near supercritical conditions may have a density of 0.2 to 0.7, or more particularly 0.3 to 0.4, grams per cubic centimeter. Thus, the contacting step may be carried out at a pressure above, below, or equal to the critical pressure of the solvent. Those skilled in the art will appreciate that, when the solvent is a mixture of different molecules, the critical pressure of the solvent will actually be a pressure range, with the range depending on the composition of the solvent.

In general, with common catalysts, the contacting step may be carried out at a temperature of from 150 or 200 degrees Centigrade up to 300 or 400 degrees centigrade. The pressure will generally be from 10 to 30 atmospheres up to 80 or 100 atmospheres. Ideally, the conditions of the contacting step should be as close as possible to the conditions of the bubble column reactor, as discussed in greater detail above. The hydrocarbon solvent and the output slurry are typically contacted at a ratio, by volume, of anywhere from about one to one hundred parts of the hydrocarbon solvent to one part of the output slurry. Thus, the volume of solvent in the contacting step (e.g., contained in the contactor) is generally greater than the volume of slurry in the contacting step.

In overview, a preferred embodiment of the method of the present invention, carried out in an apparatus as described above, is as follows (note that, while the process is described in a sequential, stepwise fashion, the process is usually carried out as a continuous process). First, a synthesis gas is reacted in the presence of Fischer-Tropsch catalyst particles in a Fischer-Tropsch slurry bubble column reactor to produce a liquid hydrocarbon product (gaseous product also typically being produced as well) in the reactor. An output slurry composed of Fischer-Tropsch catalyst particles and the liquid hydrocarbon product is then collected from the reactor. Next, a compressed hydrocarbon solvent is contacted with the output slurry, with this contacting step being carried out at a temperature and pressure wherein the liquid hydrocarbon product is soluble in the solvent. This contacting step produces a concentrated slurry phase containing the catalyst, and an enriched solvent phase containing liquid hydrocarbon product. The concentrated slurry is then separated from the enriched solvent and recycled to the Fischer-Tropsch bubble column reactor.

In general, for a given solvent, the solubility of a product in the solvent decreases as the molecular weight of the product increases, i.e., high molecular weight products are less soluble in a given solvent than low molecular weight products. Thus, if there is only one stage of product reacovery, there will be a tendency to "over-recover" the light products and "under-recover" the heavy products. This will cause the viscosity of the slurry being returned to the reactor to be higher than the viscosity of the slurry in the reactor, leading to an increase with time of the slurry in the reactor, eventually causing problems with the operability of the reactor.

The enriched solvent is passed to a separator and a first fraction of the liquid hydrocarbon product is separated therefrom. This separating step forms a first hydrocarbon product fraction and a first depleted solvent. This separating step may be carried out by any suitable means, such as (i) reducing the pressure of the enriched solvent at an essentially constant temperature, (ii) raising the temperature of the enriched solvent at essentially constant pressure, or (iii) both reducing the pressure and raising the temperature of said enriched solvent. The first hydrocarbon product fraction typically contains not more than 100 to 200 parts per million of the Fischer-Tropsch catalyst particles, and preferably contains not more than 10 to 50 parts per million of the Fischer-Tropsch catalyst particles.

At least a portion of the first depleted solvent is then compressed to form a compressed hydrocarbon solvent and recycled to the contacting step.

The depleted solvent stream is then passed to a second separating step and a second fraction of the liquid hydrocarbon product is separated therefrom to form a second hydrocarbon product fraction and a second depleted solvent. The second product recovery separating step may be carried out in the same manner as the first product recovery separating step, and as with the first hydrocarbon product fraction, and the second hydrocarbon product fraction preferably contains not more than 100 to 200 parts per million of the Fischer-Tropsch catalyst particles, and more preferably contains not more than 10 to 50 parts per million of said Fischer-Tropsch catalyst particles. If desired, a third liquid hydrocarbon product fraction with like catalyst particle composition can be obtained in like manner to the first and second product fractions, and so on for still additional fractions if desired. At least a portion of the second depleted solvent is then compressed to form a compressed hydrocarbon solvent and recycled to the contacting step.

In a particularly preferred embodiment, a portion of the second hydrocarbon, or a subsequent, product fraction (i.e., any other product fraction subsequent to the first fraction if there are more than two separating steps; a portion of a low molecular weight product fraction) is recycled to the bubble column reactor, so that the viscosity of the slurry in the reactor is maintained at a predetermined range. By returning such lower molecular weight components to the reactor, this step advantageously compensates for the tendency of Fischer-Tropsch reactions to favor the production of lower molecular weight components, and compensates for the tendency of the solvent to extract more lower molecular weight hydrocarbons from the slurry than are produced by the reaction, relative to higher molecular weight components produced by the reaction. If desired, the viscosity of the slurry in the bubble column reactor can be monitored or detected by means of a suitable viscosity sensor, so that the portion recycled is selected to control the viscosity of the slurry in the bubble column reactor. In the alternative, the amount of the hydrocarbon product returned can simply be a predetermined and preset amount.

The foregoing is illustrative of the present invention, and not to be construed as limiting thereof. It will be appreciated that the basic apparatus and process steps described above may be modified and added to in many ways without departing from the basic concept of the invention described herein. Accordingly the invention is to be defined by the following claims, with equivalents of the claims included therein.

That which is claimed is:

1. An apparatus for making a hydrocarbon product by a Fischer-Tropsch reaction, comprising:

a Fischer-Tropsch slurry bubble column reactor for reacting a synthesis gas in the presence of Fischer-tropsch catalyst particles to produce a slurry comprising liquid hydrocarbon product and Fischer-Tropsch Catalyst particles in said reactor;

a slurry output line connected to said slurry bubble column reactor for providing an output of said slurry;

a compressed hydrocarbon solvent supply;

contacting means connected to said slurry output line and said compressed hydrocarbon solvent supply for contacting said compressed hydrocarbon solvent with said output slurry at a temperature and pressure wherein said liquid product is soluble in said solvent to form a concentrated slurry phase containing said catalyst and an enriched solvent phase containing liquid hydrocarbon product;

first separating means connected to said contacting means for separating said concentrated slurry from said enriched solvent; and recycling means connected to said first separating means for recycling said concentrated slurry to said Fischer-Tropsch slurry bubble column reactor.

2. An apparatus according to claim 1, further comprising second separating means connected to said first separating means for separating a first fraction of said liquid hydrocarbon product from said enriched solvent to form a first hydrocarbon product fraction and a first depleted solvent.

3. An apparatus according to claim 1, wherein said contacting means comprises a mixer.

4. An apparatus according to claim 1, wherein said first separating means comprises a settler.

5. An apparatus according to claim 1, wherein said first separating means comprises a centrifuge.

6. An apparatus according to claim 1, wherein said contacting means and said first separating means together comprise a continuous countercurrent contactor.

* * * * *